US009803230B2

(12) United States Patent
Gundling (10) Patent No.: US 9,803,230 B2
(45) Date of Patent: Oct. 31, 2017

(54) ONE-STEP PROCEDURE FOR THE PURIFICATION OF NUCLEIC ACIDS (71) Applicant: Abbott Molecular Inc., Des Plaines, IL (US)

(72) Inventor: Gerard J. Gundling, Lake Forest, IL (US)

(73) Assignee: Abbott Molecular Inc., Des Plaines, IL (US)

(*) Notice: Subject to any disclaimer, the term of this patent is extended or adjusted under 35 U.S.C. 154(b) by 34 days.

(21) Appl. No.: 14/212,880

(22) Filed: Mar. 14, 2014

(65) Prior Publication Data

US 2014/0272944 A1    Sep. 18, 2014

Related U.S. Application Data (60) Provisional application No. 61/789,622, filed on Mar. 15, 2013.

(51) Int. Cl.
C07H 21/00 (2006.01)
C12N 15/00 (2006.01)
G01N 1/34 (2006.01)
C12Q 1/68 (2006.01)
C12N 15/10 (2006.01)

(52) U.S. Cl.
CPC ....... C12Q 1/6806 (2013.01); C12N 15/1006 (2013.01); C12N 15/1013 (2013.01)

(58) Field of Classification Search
CPC .... C12Q 1/68; C12Q 1/6806; C12N 15/1006; C12N 15/10013; C12N 15/1003; G01N 1/34
See application file for complete search history.

(56) References Cited

U.S. PATENT DOCUMENTS

| | | | |
|---|---|---|---|
| 4,777,145 A | 10/1988 | Luotola et al. | |
| 5,075,430 A * | 12/1991 | Little | C12N 15/1006 423/335 |
| 5,234,809 A * | 8/1993 | Boom | C07H 21/00 422/504 |
| 5,279,936 A | 1/1994 | Vorpahl | |
| 5,455,344 A | 10/1995 | Harper et al. | |
| 5,637,687 A * | 6/1997 | Wiggins | C12N 15/1003 435/270 |
| 5,705,628 A * | 1/1998 | Hawkins | C12N 15/1013 252/62.51 R |
| 5,770,388 A | 6/1998 | Vorpahl | |
| 6,117,398 A | 9/2000 | Bienhaus et al. | |
| 6,180,778 B1 * | 1/2001 | Bastian | C12N 15/1006 536/25.3 |
| 6,992,782 B1 * | 1/2006 | Yardumian | G06F 3/1206 358/1.13 |
| 8,008,475 B1 * | 8/2011 | Bastian | C12Q 1/6806 210/650 |
| 8,734,364 B1 * | 5/2014 | Mantzaris | A61B 5/4362 600/572 |
| 2003/0083339 A1 * | 5/2003 | Tamura | A61K 31/401 514/263.4 |
| 2004/0111760 A1 * | 6/2004 | Chia | C12N 9/1029 800/278 |
| 2004/0178073 A1 * | 9/2004 | Kozulic | G01N 27/4473 204/462 |
| 2005/0059024 A1 * | 3/2005 | Conrad | C12N 15/1003 435/6.12 |
| 2005/0106577 A1 * | 5/2005 | Akhavan-Tafti | C07H 21/04 435/6.16 |
| 2005/0208037 A1 * | 9/2005 | Dashnamoorthy | A61K 31/704 424/94.4 |
| 2005/0208510 A1 * | 9/2005 | Latham | C12N 15/1006 435/6.12 |
| 2005/0239068 A1 * | 10/2005 | Bosnes | G01N 33/54306 435/6.18 |
| 2007/0065824 A1 | 3/2007 | Gutig | |
| 2009/0048439 A1 * | 2/2009 | Weisburg | C12N 15/1006 536/25.41 |
| 2009/0215125 A1 * | 8/2009 | Reed | B01L 3/5027 435/91.2 |
| 2009/0277791 A1 * | 11/2009 | Vu | G01N 33/559 204/461 |
| 2010/0140110 A1 * | 6/2010 | Kim | B01L 3/502761 205/775 |
| 2011/0172409 A1 * | 7/2011 | Han | C12N 15/1006 536/25.4 |
| 2011/0245483 A1 * | 10/2011 | Euting | C12N 15/1013 536/25.41 |
| 2013/0273552 A1 | 10/2013 | Ohashi | |

FOREIGN PATENT DOCUMENTS

| | | | |
|---|---|---|---|
| CN | 1617938 A | 5/2005 | |
| EP | 0389063 A2 | 9/1990 | |
| EP | 0905520 A1 | 3/1999 | |

(Continued)

OTHER PUBLICATIONS

Eads et al., Methylight: a high-throughput assay to measure DNA methylation. Nucleic Acids Research 28(8) : e32 (2000).—Provided in U.S. Appl. No. 14/209,225.*
Heid et al.,Real Time Quantitative PCR. Genome Research 6 : 986 (1996).—Provided in U.S. Appl. No. 14/209,225.*
Herman et al.,Methylation-specific PCR: a novel PCR assay for methylation status of CpG islands. PNAS93 : 9821 (1996).—Provided in U.S. Appl. No. 14/212,880.*
Kopreski et al.,Detection of mutant K-ras DNA in plasma or serum of patients with colorectal cancer. British J. of Cancer 76 (10) : 1293 (1997).—Provided in U.S. Appl. No. 14/209,225.*
Maire et al., Differential diagnosis between chronic pancreatitis and pancreatic cancer: value of the detection of KRAS2 mutations in circulating DNA. British J. of Cancer 87:551 (2002).—Provided in U.S. Appl. No. 14/209,225.*

(Continued)

Primary Examiner — Ethan C Whisenant
(74) Attorney, Agent, or Firm — Pierce Atwood LLP; Kevin M. Farrell; David J. Wilson (57) ABSTRACT The present invention is a new and non-obvious method for the improved and simplified purification of nucleic acids.

25 Claims, 4 Drawing Sheets (56) References Cited

FOREIGN PATENT DOCUMENTS

| | | |
|---|---|---|
| EP | 2418018 A2 | 2/2012 |
| JP | 200431792 A | 1/2004 |
| JP | 2009519023 A | 5/2009 |
| WO | 8604684 | 8/1986 |
| WO | 8701206 | 2/1987 |
| WO | 8905456 | 6/1989 |
| WO | 9426414 | 11/1994 |
| WO | 9609308 | 3/1996 |
| WO | 9609379 A1 | 3/1996 |
| WO | 9641811 | 12/1996 |
| WO | 9702357 | 1/1997 |
| WO | 0171732 A2 | 9/2001 |
| WO | 0194572 A1 | 12/2001 |
| WO | 2004072228 A3 | 8/2004 |
| WO | 2005021748 A1 | 3/2005 |
| WO | 2005070545 A1 | 8/2005 |
| WO | 2012061726 A2 | 5/2012 |
| WO | 2012086243 | 6/2012 |
| WO | 2013013030 A2 | 1/2013 |

OTHER PUBLICATIONS

Saiyed et al., Application of magnetic particles (Fe3O4) for isolation of genomic DNA from mammalian cells. Analytical Biochemistry 356 : 306 (2006). Provided in U.S. Appl. No. 14/212,880.*

Saiyed et al., Extraction of DNA from agarose gel using magnetic nanoparticles (magnetite or Fe3O4). Analytical Biochemistry 363 : 288 (2007). Provided in U.S. Appl. No. 14/212,880.*

Su et al., Human Urine Contains Small, 150 to 250 Nucleotide-Sized, Soluble DNA Derived from the Circulation and May Be Useful in the Detection of Colorectal Cancer. J. of Molecular Diagnostics 6 (2) • 101 (2004).—Provided in U.S. Appl. No. 14/209,225.*

Tan et al., Review Article : DNA, RNA, and Protein Extraction: The Past and the Present Journal of Biomedicine and Biotechnology 2009: 10 pages.—Provided in U.S. Appl. No. 14/212,880.*

Taylor et al. Application of magnetite and silica-magnetite composites to the isolation of genomic DNA. Journal of Chromatogrphy A 890 : 159 (2000).—Provided in U.S. Appl. No. 14/212,880.*

Yang et al. Magnetite-Containing Spherical Silica Nanoparticles for Biocatalysis and Bioseparations. Analytical Chemistry 76 : 1316 (2004).—Provided in U.S. Appl. No. 14/212,880.*

Mehta et al.,Direct binding of protein to magnetic particles. Biotechnology Techniques 11(7) :493 (1997).*

Birnboim, et al. "A rapid alkaline extraction procedure for screening recombinant plasmid DNA" Nucleic Acids Research; Aug. 3, 1979; vol. 7; No. 6; pp. 1513-1523.

D.ish-Horowicz, et al. "Rapid and efficient cosmid cloning" Nucleic Acids Research; May 18, 1981; vol. 9; No. 13; pp. 2989-2998.

Dissing, et al. "A five minute procedure for extraction of genomic DNA from whole blood, semen and forensic stains for PCR" Department of Forensic Genetics, Institute of Forensic Medicine, University of Copenhagen; 1996; pp. 269-271.

Klintschar, et al. "Evaluation of an Alkaline Lysis Method for the Extraction of DNA from Whole Blood and Forensic Stains for STR Analysis" Journal of Forensic Sciences; 2000; vol. 45; No. 3; pp. 669-673.

Herzer "Molecular Biology Problem Solver: A Laboratory Guide" Willy-Liss, Inc.; Chapter 7 DNA Purification by Sibylle. Herzer, 2001; pp. 167-195.

Bordelon, et al. "Development of a Low-Resource RNA Extraction Cassette based on Surface Tension Valves" Applied Materials & Interfaces; 2011; vol. 3; pp. 2161-2168.

Berry, et al. "One-step purification of nucleic acid for gene expression analysis via Immiscible Filtration Assisted by Surface Tension (IFAST)" Lab Chip; 2011; vol. 11; pp. 1747-1753.

Den Dulk, et al. "Magneto-capillary valve for integrated purification and enrichment of nucleic acids and proteins" Lab Chip; 2013; vol. 13; pp. 106-118.

Karle, et al. "Continuous microfluidic DNA extraction using phase-transfer magnetophoresis" Lab Chip; 2010; vol. 10; pp. 3284-3290.

Bulletin of education and research; Nihon University School of Dentistry at Matsudo; 2005; vol. 8; pp. 1-8.

* cited by examiner

Lysis with gel and elution on top.

FIG. 1A

Particles captured

FIG. 1B

Sliding particles up the side of the tube.

FIG. 1C

Sliding particles up the elution buffer.

FIG. 1D

Elution by moving the particles through the elution buffer using the magnets.

FIG. 1E

Moving particles back down into the gel prior to removal of eluate.

ONE-STEP PROCEDURE FOR THE PURIFICATION OF NUCLEIC ACIDS

BACKGROUND

Nucleic acid purification typically consists of a lysis step to release nucleic acids from a sample, the binding of the nucleic acids to a solid matrix, the washing of the matrix to remove contaminating substances and the elution of the nucleic acids from the matrix in a buffer. The process is complex, particularly in the washing of the matrix in the removal of contaminants. Solutions must be added to the matrix which will remove contaminants but not the nucleic acids and then these solutions must be removed prior to the elution of the nucleic acids from the matrix. If magnetic particles are used as the solid matrix, they typically must be captured after the binding step, separated from the lysis-binding solution, either by capture and removal of the particles from the solution or by immobilization of the particles and removal of the lysis-binding solution, and then released into a wash solution. Following the wash the particles must be captured again and separated from the wash solution. See, e.g., Alderton, R. P., et al., Anal. Biochem. (1992) 201:166-169 and WO 91/00212. Some protocols require several wash steps using several different wash solutions. After the particles have been washed, they must be re-suspended in an elution buffer to release the nucleic acids from the particles. Further, these procedures are often not selective for nucleic acids. Rather, a variety of solid and dissolved substances are agglutinated as well.

Other protocols require the precipitation of the nucleic acid with, for example, ethanol. The precipitated nucleic acid must then be washed and resolubilized. Chromatographic procedures also exist for the isolation of nucleic acid (see, e.g., EP 0 658 164) but these procedures also require multiple steps and washes.

The prior art SCODA (Synchronous Coefficient of Drag Alteration) system by Boreal Genomics, Inc. (Los Altos, Calif.) uses a pulsed electronic field to focus nucleic acids into a point but this is typically pre-purified material that may be very dilute. The oil-gate system developed by Kelso at Northwestern University (Sur, et al., Immiscible Phase Nucleic Acid Purification Eliminates PCR Inhibitors with a Single Pass of Paramagnetic Particle through a Hydrophobic Liquid, J. Mol. Diag. 2012 12(5):620-628) drags the particles through oil to try to eliminate washing but the method resulted in substantial salt carry over because the oil left a large droplet of lysis solution around the particles which resulted in a great deal of salt carryover. Thus, additional processing was necessary when using this system.

It can be seen that the methods for the isolation/purification of nucleic acids that are considered state of the art have certain disadvantages. Such disadvantages relate to, e.g., purity, selectivity, recovery rate, laboratory safety and convenience, as well as to the speed of the isolation/purification process. In other words, known prior art procedures require multiple steps and often result in loss of target nucleic acid due to numerous steps and/or alteration of target nucleic acid (for example, loss of modifying groups due to repeated harsh treatment conditions).

Thus, the problem to be solved is to provide a simpler procedure for isolating nucleic acids from a sample that will save time and reagents and help prevent the loss of target and/or modification of the target during processing.

SUMMARY OF THE INVENTION

The invention relates to the use of a gel to separate the lysis-binding solution from an elution buffer. Particles are used to capture nucleic acids in the lysis-binding solution. The particles are magnetic and are concentrated using a magnetic field. Specifically, the particles are drawn by a magnetic field through a gel that removes contaminants, and the concentrated particles are re-suspended in an elution buffer. The process is extremely simple. The gel separates the lysis-binding solution from the elution buffer and limits or eliminates mixing between the two. The movement of the particles through the gel removes contaminants and salts. Contaminants are removed by the passage through the gel (i.e., they are "squeegeed" out). Salts are diluted out by passing through the gel. The particles then pass directly into the elution buffer where the nucleic acids are released. The magnetic particles can then be drawn back into the gel or separated from the elution buffer by centrifugation or settling (gravity). This process has been shown to successfully purify HCV viral RNA from a plasma sample using a real-time PCR assay to detect the hepatitis C virus (HCV viral) RNA.

The present invention contemplates a method of removing lysis buffer components from a nucleic acid sample, the method comprising: providing a specimen comprising or suspected of comprising nucleic acids, contacting the specimen with one or more lysis reagents, contacting the specimen with a solid substrate for a length of time and under conditions suitable for nucleic acids in the specimen to bind to the solid substrate and causing the solid substrate bound with nucleic acids, if nucleic acid is present in the specimen, to pass through an aqueous-based separation gel. The present method is useful when the lysis buffer contains salts in a concentration greater than about 1 molar. The solid substrate may be a microparticle and the microparticle may be from about 0.1 nm to about 5 nm in diameter or from about 0.8 nm to about 5 nm in diameter. Further, the microparticle may be magnetic.

The present invention further contemplates that the nucleic acids bound to the solid substrate are contacted with an elution buffer after passing through the aqueous gel which elutes nucleic acids from the solid substrate. Further still, the nucleic acids are not precipitated in an organic solvent or the nucleic acids may be precipitated in an organic solvent and the organic solvent may be ethanol or any other suitable organic solvent.

The present invention further contemplates that the nucleic acids bound to the solid substrate are contacted with an enzyme after passing through the aqueous gel, either before or after elution from the solid substrate. The enzyme may be a DNA polymerase or a reverse transcriptase. Further still, the nucleic acid may be sequenced on the solid substrate without dilution.

The present invention further contemplates that the nucleic acids bound to the solid substrate may be contacted with bisulfite after passing through the aqueous gel such that unmethylated cytosines are deaminated. The present invention further contemplates that at least one nucleic base in the nucleic acid may have an epigenetic modification.

The present invention still further contemplates that the nucleic acid may be bound to the solid substrate via an entity selected from the group consisting of nucleic acid hybridization, an aptamer, an antibody, an antibody fragment, biotin, avidin, and streptavidin.

The present invention contemplates a method for enriching nucleic acids from a sample, the method comprising: providing; a sample suspected of comprising nucleic acids, microparticles suitable for binding nucleic acids, and an aqueous-based separation gel, contacting the sample with the microparticles for a length of time and under conditions suitable for any nucleic acids in the sample to bind to the magnetic microparticles to create loaded magnetic microparticles; drawing the loaded microparticles through the aqueous-based separation gel with a magnetic field. The gel may be an agarose gel. The agarose gel may be at a concentration of about 0.10% to about 1.0%. The separating gel may also comprise one of more of ethanol and glycerol. The particles may also comprise a functional group suitable for binding nucleic acid.

It is further contemplated that the microparticles may be magnetic and the magnetic microparticles are, optionally at least partly coated with one or more of silica and glass. The magnetic microparticles may be spheroid although any shape is contemplated as being suitable in the present invention.

It is further contemplated that the sample may comprise lysis buffer.

DESCRIPTION OF THE FIGURES

FIG. 1(A-F) shows an exemplification of the method of the present invention as described in the Examples.

FIG. 2 shows (A) DNA amplification curves of target nucleotide sequences purified by the methods of the present invention as detailed in Example 2 and (B) internal controls.

FIG. 3 shows (A) DNA amplification curves of target nucleotide sequences purified by the methods of the present invention as detailed in Example 2 and (B) internal controls.

DETAILED DESCRIPTION OF THE INVENTION

The present methods are directed toward a one-step isolation and purification method of nucleic acids. The method is simple and easily performed by one of ordinary skill in the art. The method involves adding to a lysis solution (lysis solutions are known to those of ordinary skill in the art) and a solid substrate that binds nucleic acid (for example, iron oxide particles, magnetic particles, magnetic particles that are at least partly coated with glass, silica or the like, etc.). Nucleic acids present will bind the particles. The particles are then drawn through an aqueous gel (e.g., an agarose gel although any gel compatible with nucleic acids, for example an SDS acrylamide gel, would be suitable) with, in the case of magnetic particles, a magnetic source (i.e., a magnet) positioned outside of the assay vessel. The action of drawing the particles through the gel removes (i.e., "squeegees") non-soluble contaminants and dilutes soluble contaminants (e.g., salts). The particles enter an elution buffer after leaving the gel. The nucleic acid is released in the elution buffer. The magnetic particles can then be drawn back into the gel or allowed to settle out (or centrifuged out after removal of the elution buffer from the gel surface). The method is typically performed in a tube wherein the gel is layered over the lysis buffer and the elution buffer is layered over the gel. Optionally, a non-eluting buffer can be layered over the gel and the nucleic acids eluted from the particles at a later time, if desired. The elution buffer may or may not comprise an organic solvent (such as ethanol).

Typical lysis buffers comprise salts. Salts typically found in lysis buffers include, but are not limited to guanidinium thiocyanate (GITC) (typical range of 0.5 M to 4.0 M), NaCl (typical range of up to 0.1 M and 10.5 M), Lysis buffers also typically contain a buffer (for example, Tris-HCl; typical concentration of about 25 mM, about pH 7 to about pH 8, or other suitable buffer known to one of ordinary skill in the art) and detergents (for example, NP-40, Tween™, Triton™-X, polysorbates, deoxycholate, sodium deoxycholate and sodium dodecyl sulfate (SDS); concentrations typically used range from about 0.1% to about 2.0%).

The present invention is not limited to any specific sample or sample type. For example, sample materials may include bodily fluids including plasma, serum, blood, spinal fluid, semen, vaginal fluids, sputum and saliva, cerebrospinal fluid, lymphatic fluid and digestive fluids. Other sample materials may include isolated or enriched cell populations and tissues. Samples may be fresh or fixed (preserved). Fixed samples may be embedded (for example, paraffin embedded). Further, samples may be obtained from archeological digs, i.e., prehistoric tissues such as bones may yield nucleic acids that can be enriched or isolated by the methods of the present invention. Certain sample types may require pretreatment to, for example, concentrate the sample (by, for example, centrifugation of suspended cells) or break apart large sample sources (for example, grinding of bones or digestive breakdown of tissues). Such pretreatments are primary to obtain starting materials that are more easily workable by the methods of the present invention.

The gels used in the present invention may be at a concentration of about 0.1% to about 1.0%, about 0.15% to about 0.75%, about 0.2% to about 0.50%.

In the present specification it is understood that the term "a nucleic acid" denotes at least one nucleic acid. Furthermore, the term "a nucleic acid" also may indicate a mixture of nucleic acids. The term "nucleic acid" encompasses RNA, DNA, or both. Further, as used herein, "nucleic acid" or "NA" refers to both a deoxyribonucleic acid and a ribonucleic acid. As used herein, "nucleic acid sequence" refers to the order or sequence of deoxyribonucleotides or ribonucleotides along a strand. They may be natural or artificial sequences and, in particular, genomic DNA (gDNA), complementary DNA (cDNA), messenger RNA (mRNA), transfer RNA (tRNA), ribosomal RNA (rRNA), hybrid sequences or synthetic or semisynthetic sequences or oligonucleotides which are modified or contain modified bases. These nucleic acids may be of human, animal, plant, bacterial or viral origin and the like. They may be obtained by any technique known to persons skilled in the art, and in particular by cell lysis, the screening of libraries, by chemical synthesis or by mixed methods including the chemical or enzymatic modification of sequences obtained by the screening of libraries. They may be chemically modified, e.g. they may be pseudonucleic acids (PNA), oligonucleotides modified by various chemical bonds (for example phosphorothioate or methyl phosphonate), or alternatively oligonucleotides which are functionalized, e.g., which are coupled with one or more molecules having distinct characteristic properties.

The methods of the present invention may be altered to specifically isolate or enrich either DNA or RNA. For example, the use non-coated iron oxide as a capture particle would be selective for RNA. Silica particles or silica coated particles, for example, would be specific for DNA. However, if you make the lysis buffer 33% ethanol, silica particles, for example, will bind both DNA and RNA for total nucleic acids isolation or enrichment.

The term "substrate" denotes a substance which is substantially insoluble in an aqueous solution and on which a nucleic acid in an aqueous solution (of high ionic strength) can adsorb when the substance is added. The term "substrate" encompasses magnetically attractable particles and magnetically attractable particles such as uncoated iron oxide or coated with, for example, silica, glass, quartz or zeolites. However, the substrate need not be magnetic.

Further, the particles may comprise functional groups suitable for binding nucleic acids. Examples of such functional groups include but are not limited to proteins (or functional portions thereof), antibodies (or functional portions thereof), chemical linkers (e.g., avidin, streptavidin, via nucleic acid hybridization, an aptamer, biotin, etc.). Thus, the nucleic acid need not be bound directly to the substrate but may be bound via one or more entities, as described herein or as are known to one of ordinary skill in the art. Further, non-magnetic particles may be caused to pass though the aqueous-based gel by, for example, centrifugation (e.g., low speed centrifugation). In this embodiment, it is contemplated that the elution buffer (or saline, etc.) would be at bottom of the tube with the gel layered over the elution buffer and the lysis buffer on top of the gel. The force of the centrifugation would pull the particles down though the gel into the elution buffer. In another embodiment, the tube is set up as with using a magnetic force (lysis buffer on bottom, elution buffer on top) and the tube is capped and inverted before centrifugation. Further, other means for moving the microparticles though the gel are contemplated. For example, charged particles may be drawn through the gel by electrophoretic-type methods. Further still, if the particles are allowed to settle (or centrifuged to the level of the gel) and the lysis buffer is removed, the microparticles can be pushed through the gel with a device similar to a French press.

The substrate can be of any shape including, but not limited to, spherical, elliptical, oblong, rod shaped, spiral and amorphous. The substrate of the present invention is not limited by size but is preferably about 0.2 mm or less, 0.02 mm or less, 2.0 μm or less, 200 nm or less, 20 nm or less and 2 nm or less in the largest diameter. The substrate of the present invention may also be about 0.1 nm to about 5 nm and may be about 0.8 nm to about 5 nm in diameter. Further, it is understood that a substrate, when dispersed in a liquid phase such as an aqueous solution, may produce a suspension or may settle out of the solution.

The terms "high ionic strength" and "high concentration" mean the ionic strength or concentration in an aqueous solution that results from dissolved salts in concentrations equal to or greater than about 1 M. Typically salts are present in the aqueous solution in concentrations of 1 to 10 M. More typical are chaotropic salts in concentrations of 1 to 8 M. In a preferred embodiment, the lysis buffer of the present invention has a salt concentration of greater than about 1 M.

The terms "low ionic strength" and "low concentration" mean the ionic strength or concentration in an aqueous solution that results from dissolved salts in concentrations less than about 1 M.

The terms "magnetic" and "magnetic particle(s)" shall refer to objects made from a material that is magnetized and/or creates its own persistent magnetic field. Although any suitable material as is known to one of ordinary skill in the art is contemplated for use in this invention, iron-based materials (e.g., iron oxide) or material in which comprise iron oxide are most frequently contemplated. In the present invention the magnetic particles (multifunctional magnetic particles; MMP) form a substrate and, while not limited by size, are preferably about 0.2 mm or less, 0.02 mm or less, 2.0 μm or less, 200 nm or less, 20 nm or less and 2 nm or less in the largest diameter. In a preferred embodiment of the present invention, the magnetic particles of the present invention are coated at least partly with glass, silica or one or more substances known to one of ordinary skill in the art to bind nucleic acids. Micro- and nano-sized magnetic particles are commercially available to one of ordinary skill in the art (e.g., Promega Corp., Madison, Wis.; Life Technologies, Grand Isle, N.Y.; Bangs Laboratories, Fishers, Ind.). Further, particles can be synthesized in the lab by one of ordinary skill in the art, see, for example, Starmans L W, et al., Iron Oxide Nanoparticle-Micelles (ION-Micelles) for Sensitive (Molecular) Magnetic Particle Imaging and Magnetic Resonance Imaging, PLoS One, Epub 2013 Feb. 20; 8(2)e57335; Heitsch, Andrew T., et al., Multifunctional Particles: Magnetic Nanocrystals and Gold Nanorods Coated with Fluorescent Dye-Doped Silica Shells, Solid State Chem. 2008 July; 181(7): 1590-1599.

Methods and reagents for lysing cells and tissues for the extraction of nucleic acids are well known by those or ordinary skill in the art and any method that does not destroy the nucleic acids of the sample are suitable for use by the present invention. Further, nucleic acids suitable for isolation and purification by the present method may be obtained from fixed samples (e.g., formalin or glutaraldehyde fixed samples), embedded samples (e.g., paraffin embedded samples) and from reaction vessels containing solutions or suspensions of synthesized nucleic acids.

Nucleic acids enriched, isolated or purified by the methods of the present invention may be used in any conventional method known to those of ordinary skill in the art because the methods of the present invention do not alter the nucleic acids in any way that may be detrimental to their subsequent use. For example, the nucleic acids may be sequenced, amplified by PCR, used in expression vectors, etc. In this regard, the nucleic acids may be contacted with enzymes such as, for example, a DNA polymerase or a reverse transcriptase after passing through the aqueous gel. Further, this invention contemplates that the nucleic acid is sequenced on the solid substrate without dilution. Further, this invention contemplates that the nucleic acids bound to the solid substrate are contacted with bisulfite after passing through the aqueous gel such that unmethylated cytosines are deaminated. Further, this invention contemplates that at least one nucleic base in the nucleic acid has an epigenetic modification.

Kits

The present invention also contemplates kits wherein the kits contain gel solutions and/or gel ingredients (as exemplified below or equivalents as could be determined by one of ordinary skill in the art without undue experimentation), magnetic particles suitable for binding nucleic acids and instructions. Optionally, vials, reaction solutions and other items could be provided in a kit of the present invention for specific uses (e.g., the isolation of RNAs) and/or to aid the user with regard to performing the procedure.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under herein and are otherwise defined, described, or discussed elsewhere in the "Detailed Description" or elsewhere in this specification, all such definitions, descriptions and discussions are intended to be attributed to such terms. There also is no intention in the use of such terms and expressions of excluding any equivalents of the features shown and described or portions thereof.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

EXEMPLIFICATION

Example 1

The concept of the present invention is that nucleic acids can be easily purified from, for example, cell lysates or other cellular sample, by binding the nucleic acid to magnetic particles and then drawing the particles though a viscous, aqueous gel or gel solution. The first test was to see if the gel can reduce the salt level in a nucleic acid-free sample.

A 1% gel was made as follows. 50 ml of water (DNase and RNase free water) was mixed with 0.5 g Agarose-LE (Ambion #9040, although any commercially available agarose should be workable). The agarose was melted in the water in a microwave oven (although any suitable heat source will work) to make a 1% agarose solution and placed on a temp block (i.e., a heat block) set at 55° C. to keep the gel melted.

The lysis-ethanol solution was made as using 70 ml of a guanidine thiocyanate (GITC) containing lysis buffer (the lysis buffer having greater than 3M GITC, greater than 1% non-ionic detergent and with a pH above 7.0; or any lysis buffer suitable for the tissue or sample being processed that preserves nucleic acids) and 35 ml of 95% ethanol.

1 ml of the lysis buffer-ethanol solution was added to a 12 mm×75 mm polypropylene tube along with 0.5 ml of water to represent a sample addition. 50 microliters of silica coated magnetic microparticles (Abbott laboratories, Abbott Park, Ill., mMicroparticlesDNA) were also added to the lysis mixture.

2 ml of the melted agarose was gently floated on top of the lysis buffer and let cool to set. After hardening, the surface of the gel was washed to remove any residual guanidine that may have gotten on top of the gel by adding 500 microliters of water (above) to the surface of the gel and then removing the wash. 200 microliters of water (above) was then added to the top of the gel to represent elution buffer.

The magnetic particles (MMP) were captured with a magnet by placing a magnet on the side of the tube in the region of the lysis buffer. An alternative approach is to place a greater magnetic source directly above the tube. The magnet was then slowly drawn up the side of the tube with the magnetic field pulling the magnetic particles along. The magnetic particles smeared out somewhat while passing through the gel. The collected particles were on the side of the tube and as the bolus of particles moved up the tube the gel was displaced by the particles. A channel was formed where the particles moved through the gel. It may be possible to position a magnet such that the particles would be drawn up directly through the center of the gel but the position of the magnet does not seem to matter based on the results obtained.

The magnetic particles were moved through the gel layer to the water layer and mixed back and forth by moving the magnet from one side to the other. This was done several times to mix the particles in the water. The particles were then captured by placing the magnet on the side of the tube and drawn back into the gel such that they were removed from the top water layer. See, FIG. 1A-F. The water layer was removed and placed into a microfuge tube. Absorption readings were taken at A 230, 260, 280 and 400 on a Beckman DU-640 spectrophotometer although any commercial spectrophotometer will work. The instrument was blanked with water and the samples were read.

Readings taken at A 230. Undiluted sample gave a reading of 2.8194 which is too high for an accurate reading for this particular spectrophotometer. The sample was diluted 1/40 with water and reread. The reading was 1.7268 with the 40× dilution. A factor of 0.6× was used to convert A230 to mM GITC. 1.7268×40×0.6=41.4 mM GITC. This concentration of GITC in the sample would be acceptable. Several assays have been tested and show a tolerance to GITC up to 50 mM in the reaction. The assays of interest use and 1:1 sample volume:assay mix ratio and the 41.4 mM GITC in the sample would equal about 20 mM GITC in an assay.

The test was repeated and this time the MMP were drawn up through the gel while rotating the gel increasing the distance that the particles traveled. Spectrophotometer measurement were made using a 1/50 dilution of the sample in water. The absorbance at A230 was 0.8792. 0.8792×50×0.6=26.4 mM GITC in the sample which is an acceptable range. This method was next tested with samples containing nucleic acid.

Example 2

In this experiment a known quantity of nucleic acid was used in the sample. The nucleic acids tested were the Calibrator B from the Abbott RealTime™ HCV assay and the HCV Internal Control used in the assay extractions. The Calibrator B is an RNA sample containing HCV sequences at a concentration of approximately 10,000,000 Iu/ml (international units per milliliter) in human plasma. The internal control is also an RNA molecule used to test the extraction performance of the sample preparation systems used to extract HCV for testing. The presence of glycerol and ethanol in the gel was also tested to determine if they might have any effect on the extraction. The presence of ethanol may help retain the nucleic acids on the particles and the glycerol may change the density of the gel.

The gels were made up as follows using Ambion Agarose-LE #9040 lot 064P80B. Three reagent bottles with 25 ml of water in each were used to make the different gels. The water was DNase and RNase free water. Agarose (Ambion Agarose-LE #9040 lot 064P80B) was added to each bottle as follows.

0.05 gm agarose to bottle 1 to make a 0.2% gel.
0.10 gm agarose to bottle 2 to make a 0.4% gel.
0.15 gm agarose to bottle 3 to make a 0.6% gel.

The agarose was melted in the microwave and then the bottles were placed on top of the temp block heated to 55° C. to keep melted.

The Hepatitis C viral Calibrator B (Abbott Laboratories, Abbott Park, Ill.; this is a known quantity of HCV nucleic acid in a negative human serum) and Internal Control (Abbott Laboratories, Abbott Park, Ill.) was first extracted with the lysis-buffer ethanol mix and captured on magnetic particles as follows. The lysis ethanol mix discussed in Example 1 was used as the lysis buffer.

The Lysis Mix Contained
10 ml of the lysis ethanol mix
5 ml of HCV Calibrator B
350 µl of HCV Internal Control
500 µl of MMP (multifunctional magnetic particles)
The mix was put on a rocker plate at room temperature for 12 minutes.

During the lysate incubation, nine 15 ml tubes were set up as below.

| Tube | Agarose | water | ethanol | glycerol | Final Agarose concentration |
|---|---|---|---|---|---|
| 1 | 4 ml of 0.2% | 1 ml | 0 | 0 | 0.16% |
| 2 | 4 ml of 0.4% | 1 ml | 0 | 0 | 0.32% |
| 3 | 4 ml of 0.6% | 1 ml | 0 | 0 | 0.48% |
| 4 | 4 ml of 0.2% | 0 | 1 ml | 0 | 0.16% |
| 5 | 4 ml of 0.4% | 0 | 1 ml | 0 | 0.32% |
| 6 | 4 ml of 0.6% | 0 | 1 ml | 0 | 0.48% |
| 7 | 9 ml of 0.2% | 0 | 0 | 1 ml | 0.18% |
| 8 | 9 ml of 0.4% | 0 | 0 | 1 ml | 0.36% |
| 9 | 9 ml of 0.6% | 0 | 0 | 1 ml | 0.54% |

The glycerol content was set at 10%. At 20% glycerol, the agarose was denser than the lysis buffer and sank to the bottom of the tube.

After the lysis incubation was complete, the samples were extracted using the gel technique as follows. 1.5 ml of the lysate was put into each of 9 tubes (12 mm×75 mm polypropylene). 2 ml of each agarose mix was gently put on top and let harden (about 4° C. for ~10 minutes). 1 ml water was out on top of all tubes to remove any trace of lysis. The condition with the lowest amount of agarose and ethanol started to float above the water wash and the sample (#2) was not further tested. The water was removed from the top of the gels and 200 µl of water was added to the top of all gels for elution. The magnetic particles were captured on the side of the tube with a magnet and drawn up through the gel to elution buffer as described in example 1. The magnetic particles were then moved the particles back and forth in the elution buffer about 20 times using the magnet to draw them from one side of the tube to the other. The particles were drawn back into the gel as described above. The elution buffer was then removed and put into a microfuge tube.

From each condition a 10 µl sample was taken and dilute with 490 µl of water. The absorption was read in a spectrophotometer (Beckman DU-640) at 230 nm to determine GITC carryover as described in example 1.
The instrument was blanked with water and then the samples were read.

| Sample | A230 | mM GITC | Dilution | Final GITC (mM) |
|---|---|---|---|---|
| 1 | 0.3693 | 0.210919 | 50 | 10.54595 |
| 2 | not tested | | | |
| 3 | 0.4904 | 0.282627 | 50 | 14.13134 |
| 4 | 0.3316 | 0.188595 | 50 | 9.429773 |
| 5 | 0.4461 | 0.256395 | 50 | 12.81975 |
| 6 | 0.8110 | 0.472466 | 50 | 23.62328 |
| 7 | 0.5354 | 0.309273 | 50 | 15.46364 |
| 8 | 0.5223 | 0.301516 | 50 | 15.07579 |
| 9 | 0.5418 | 0.313063 | 50 | 15.65313 |

All the samples have GITC concentrations below 25 mM.

The samples were then tested for the presence of the HCV and Internal Control sequences using the Abbott RealTime™ HCV assay. A mastermix was made using the three components of the Abbott RealTime™ HCV assay code 4J86-90. The 320 microliters of Activator and 948 microliters of Oligo mix were added to the preloaded enzyme bottle and gently mixed by pipetting. 25 microliters of the mastermix was then mixed with 25 microliters of each eluated sample in a well of a PCR plate. 25 microliters of this mixture was then transferred to a Cepheid Tube and cycled using a Cepheid (Sunnyvale, Calif.) SmartCycler® with the following program, below.

| Temp C. | Time seconds |
|---|---|
| Step 1 for 1 cycle | |
| 55 | 1200 |
| Step 2 for 4 cycles | |
| 95 | 20 |
| 46 | 30 |
| 68 | 20 |
| Step 3 for 6 cycles | |
| 92 | 20 |
| 60 | 30 |
| 68 | 20 |
| Step 4 for 37 cycles | |
| 90 | 20 |
| 56 | 40 |
| 68 | 20 |
| 35 | 40 |

Figure 1A:
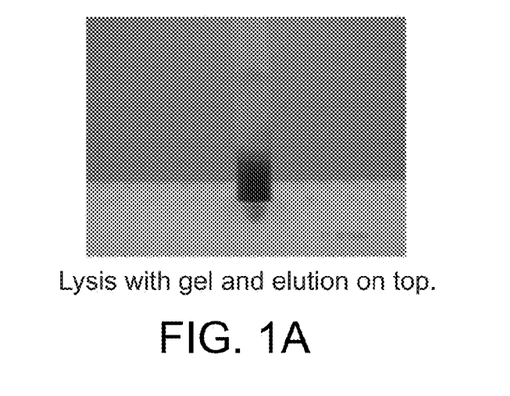
Figure 1B:
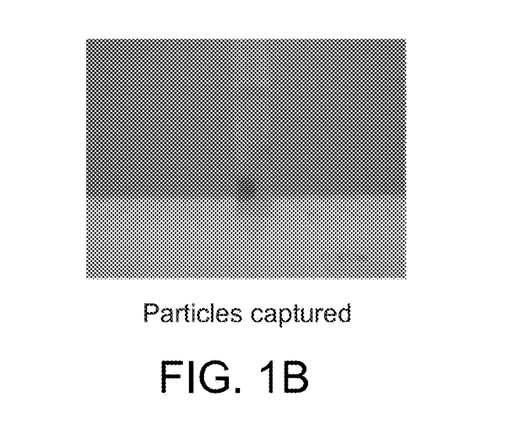
Figure 1C:
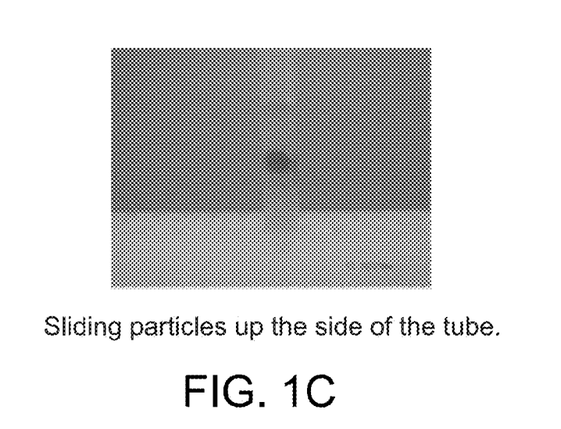
Figure 1D:
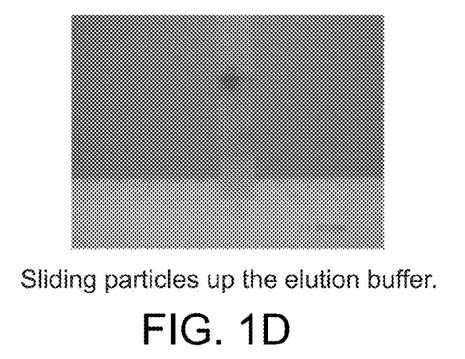
Figure 1E:
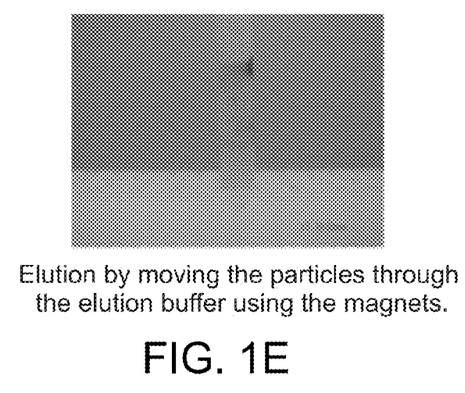
Figure 1F:
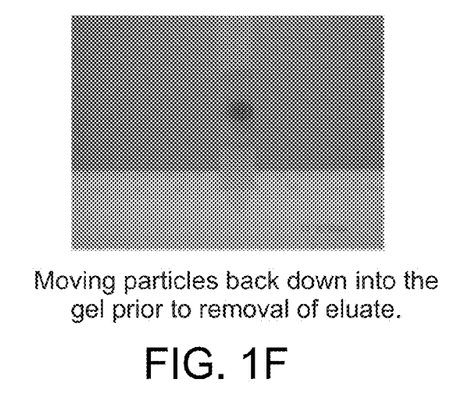
Figure 2A:
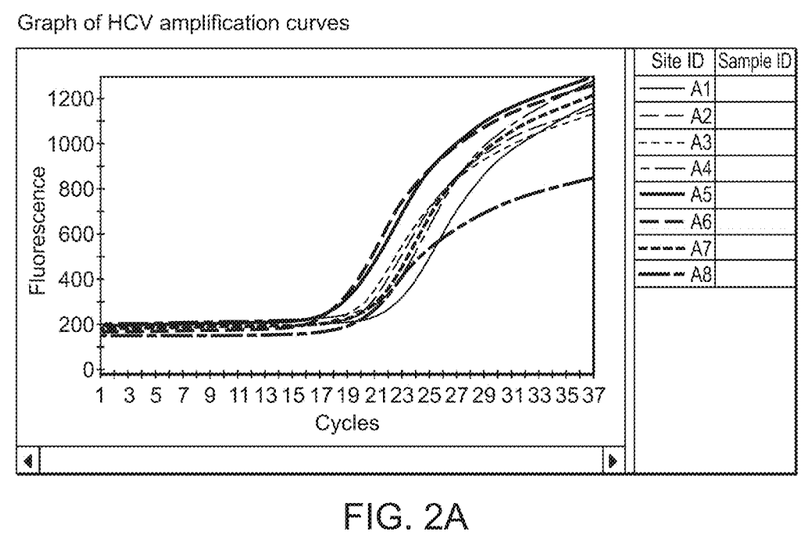
Figure 2B:
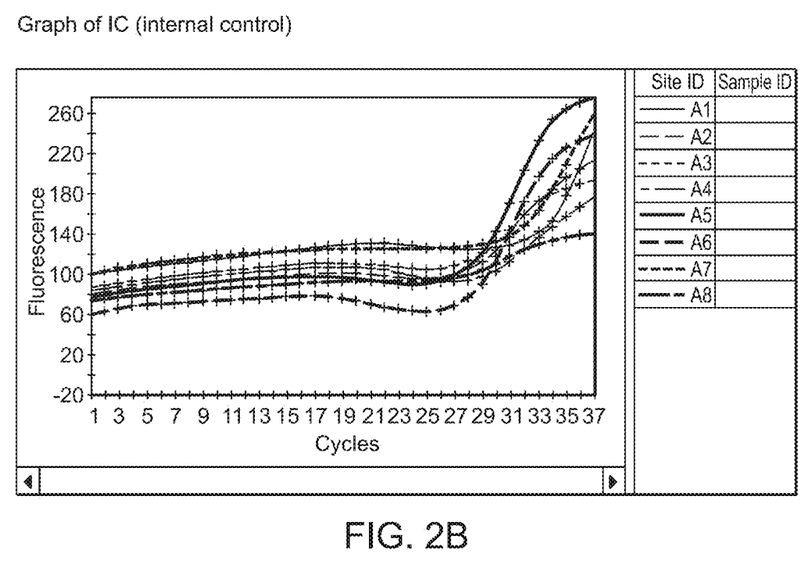

Each sample was then read.
The amplification curves are below and show that both HCV and the internal control were amplified from the eluates. FIG. 2 shows graphs of the amplification curves (A) and internal controls (B).
The second 25 microliters of each of the assay mixes were also amplified using a different program, also in the Cepheid SmartCycler.

| Temp C. | Time seconds |
|---|---|
| Step 1 for 1 cycle | |
| 55 | 1800 |
| Step 2 for 4 cycles | |
| 95 | 40 |
| 46 | 30 |
| 68 | 20 |
| Step 3 for 6 cycles | |
| 92 | 40 |
| 60 | 30 |
| 68 | 20 |
| Step 4 for 37 cycles | |
| 90 | 30 |
| 56 | 40 |
| 68 | 20 |
| 35 | 40 |

Each sample was read.

Figure 3A:
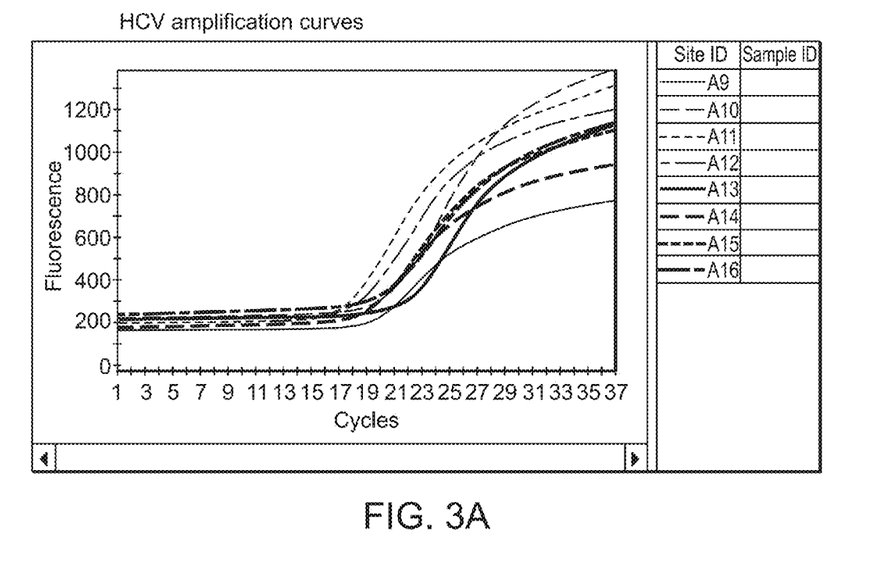
Figure 3B:
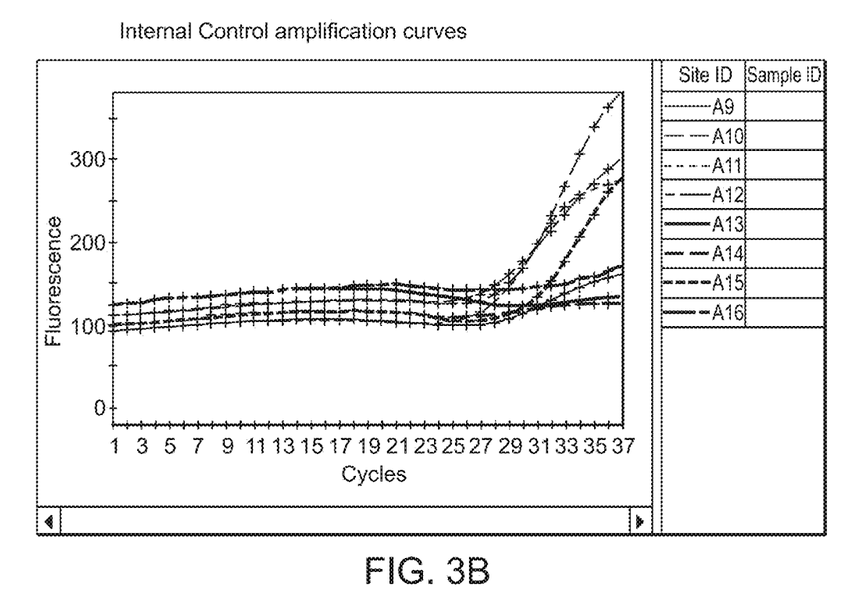

FIG. 3 shows graphs of the amplification curves (A) and internal controls (B).

These experiments demonstrate that it is possible to capture HCV on magnetic microparticles, draw the particles up through a gel, which removes high levels of GITC and other contaminants, into an elution buffer, elute the sample and use the eluted sample in a PCR assay without further purification of the nucleic acid. The extraction protocol did not use any separate washing steps.

What is claimed is:

1. A method of removing lysis buffer components from a nucleic acid sample, the method comprising
   a) providing a specimen comprising or suspected of comprising nucleic acids,
   b) contacting the specimen with one or more lysis reagents to create a lysed specimen,
   c) contacting the lysed specimen with a solid substrate for a length of time and under conditions suitable for nucleic acids in the specimen to bind to the solid substrate to create a lysed specimen with solid substrate bound nucleic acids,
   d) depositing the lysed specimen with solid substrate bound nucleic acids in a vessel, layering an aqueous-based separation gel over the lysed specimen with solid substrate bound nucleic acids and further layering a buffer over the aqueous-based separation gel, and
   e) causing the solid substrate bound nucleic acids, if nucleic acid is present in the specimen, to pass through the aqueous-based separation gel into the buffer.

2. The method of claim 1, wherein the lysis buffer contains salts in a concentration greater than about 1 molar.

3. The method of claim 1, wherein the solid substrate is a microparticle.

4. The method of claim 3, wherein the solid substrate is a microparticle from about 0.1 nm to about 5 nm in diameter.

5. The method of claim 4, wherein the solid substrate is a microparticle from about 0.8 nm to about 5 nm in diameter.

6. The method of claim 3, wherein the microparticle is magnetic.

7. The method of claim 1, wherein the nucleic acids bound to the solid substrate are contacted with an elution buffer after passing through the aqueous gel which elutes nucleic acids from the solid substrate.

8. The method of claim 7, wherein the method does not include precipitation of the nucleic acids in an organic solvent.

9. The method of claim 7, wherein the method does include precipitation of the nucleic acids in an organic solvent and the organic solvent is ethanol.

10. The method of claim 3, wherein the nucleic acids bound to the solid substrate are contacted with an enzyme after passing through the aqueous gel.

11. The method of claim 10, wherein the enzyme is a DNA polymerase or a reverse transcriptase.

12. The method of claim 10, wherein the nucleic acid is sequenced on the solid substrate without dilution.

13. The method of claim 3, wherein the nucleic acids bound to the solid substrate are contacted with bisulfite after passing through the aqueous gel such that unmethylated cytosines are deaminated.

14. The method of claim 13, further comprising determining whether at least one nucleic base in the nucleic acid has an epigenetic modification.

15. The method of claim 1, wherein the nucleic acid is bound to the solid substrate via an entity selected from the group consisting of nucleic acid hybridization, an aptamer, an antibody, an antibody fragment, biotin, avidin, and streptavidin.

16. A method for enriching nucleic acids from a sample, the method comprising:
   a) providing;
      i) a sample suspected of comprising nucleic acids,
      ii) magnetic microparticles suitable for binding nucleic acids, and
      iii) an aqueous-based separation gel,
   b) contacting the sample with the magnetic microparticles for a length of time and under conditions suitable for any nucleic acids in the sample to bind to the magnetic microparticles to create loaded magnetic microparticles;
   c) depositing the loaded magnetic microparticles in a vessel, layering an aqueous-based separation gel over the lysed loaded magnetic microparticles and further layering a buffer over the aqueous-based separation gel; and
   d) drawing the loaded magnetic microparticles through the aqueous-based separation gel with a magnetic field into a buffer.

17. The method of claim 16, wherein said separating gel comprises agarose.

18. The method of claim 17, wherein said agarose is at a concentration of about 0.10% to about 1.0%.

19. The method of claim 17, wherein said separating gel also comprises one of more of ethanol and glycerol.

20. The method of claim 16, wherein said particles comprise a functional group suitable for binding nucleic acid.

21. The method of claim 16, wherein said magnetic microparticles are at least partially coated with one or more of silica and glass.

22. The method of claim 16, wherein said magnetic microparticles are spheroid.

23. The method of claim 16, wherein said sample comprises lysis buffer.

24. The method of claim 1, wherein said buffered layered over the aqueous-based gel is an elution buffer.

25. The method of claim 16, wherein said buffered layered over the aqueous-based gel is an elution buffer.

* * * * *

UNITED STATES PATENT AND TRADEMARK OFFICE
CERTIFICATE OF CORRECTION

PATENT NO. : 9,803,230 B2
APPLICATION NO. : 14/212880
DATED : October 31, 2017
INVENTOR(S) : Gerard J. Gundling Page 1 of 1

It is certified that error appears in the above-identified patent and that said Letters Patent is hereby corrected as shown below:

In the Claims

Column 12; Claim 24; Line 1:
"wherein said buffered layered"
To:
--wherein said buffer layered--

Column 12; Claim 25; Line 1:
"wherein said buffered layered"
To:
--wherein said buffer layered--

Signed and Sealed this
Fifth Day of January, 2021

Andrei Iancu
*Director of the United States Patent and Trademark Office*